United States Patent
Graunke

(10) Patent No.: US 11,156,577 B2
(45) Date of Patent: Oct. 26, 2021

(54) METHOD AND SENSOR SYSTEM FOR MEASURING GAS CONCENTRATIONS

(71) Applicant: Sciosense B.V., AE Eindhoven (NL)

(72) Inventor: Thorsten Graunke, Reutlingen (DE)

(73) Assignee: SCIOSENSE B.V., Ae Eindhoven (NL)

( * ) Notice: Subject to any disclaimer, the term of this patent is extended or adjusted under 35 U.S.C. 154(b) by 0 days.

(21) Appl. No.: 16/414,392

(22) Filed: May 16, 2019

(65) Prior Publication Data

US 2019/0271655 A1 Sep. 5, 2019

Related U.S. Application Data

(63) Continuation of application No. 15/235,054, filed on Aug. 11, 2016, now Pat. No. 10,338,021, which is a (Continued)

(30) Foreign Application Priority Data

Feb. 11, 2014 (DE) .......................... 102014101657.2

(51) Int. Cl.
*G01N 27/12* (2006.01)
*G01N 33/00* (2006.01)

(52) U.S. Cl.
CPC ......... *G01N 27/128* (2013.01); *G01N 27/123* (2013.01); *G01N 33/0016* (2013.01)

(58) Field of Classification Search
CPC . G01N 27/128; G01N 33/0016; G01N 27/123
See application file for complete search history.

(56) References Cited

U.S. PATENT DOCUMENTS 8,265,881 B1 9/2012 Lakhotia et al.
8,852,513 B1 10/2014 Speer et al.
(Continued)

FOREIGN PATENT DOCUMENTS

DE 4040329 A1 8/1992
DE 19708770 C1 8/1998
(Continued)

OTHER PUBLICATIONS

English Machine Translation of DE 19916798 A1, Mueller et al., Nov. 2, 2000, Translated Online Aug. 2018.
(Continued)

*Primary Examiner* — David Z Huang
(74) *Attorney, Agent, or Firm* — Slater Matsil, LLP

(57) ABSTRACT

In an embodiment a sensor system includes a carrier implemented as one of a ceramic carrier, a printed circuit board or a transistor outline header, a measuring area semiconductor body implemented as a first micromechanical component, a gas sensor implemented as a second micromechanical component and including an electrode assembly, a sensitive layer and a sensor membrane that spans a recess, wherein the measuring area semiconductor body and the gas sensor are connected to each other, a further sensor with a further electrode assembly and a further sensitive layer, wherein the further sensor is a further gas sensor or a humidity sensor, and a measuring area filled by the gas sample and arranged between the measuring area semiconductor body and the gas sensor, wherein the gas in the measuring area is in contact with the gas sensor and the further sensor.

20 Claims, 7 Drawing Sheets

Related U.S. Application Data continuation-in-part of application No. PCT/EP2015/052891, filed on Feb. 11, 2015.

(56) References Cited

U.S. PATENT DOCUMENTS

| | | | |
|---|---|---|---|
| 10,338,021 B2* | 7/2019 | Graunke | G01N 27/123 |
| 2009/0084160 A1 | 4/2009 | Bristol | |
| 2010/0139365 A1 | 6/2010 | Fix et al. | |
| 2012/0036916 A1 | 2/2012 | Henshaw et al. | |
| 2013/0205870 A1 | 8/2013 | Mitsuno et al. | |
| 2013/0264660 A1 | 10/2013 | Fleischer et al. | |
| 2015/0250408 A1 | 9/2015 | Ssenyange et al. | |

FOREIGN PATENT DOCUMENTS

| | | |
|---|---|---|
| DE | 19916798 A1 | 11/2000 |
| DE | 202004018400 U1 | 2/2005 |
| DE | 102007040726 A1 | 3/2009 |
| DE | 102007057519 A1 | 10/2009 |
| DE | 102011002854 A1 | 2/2012 |
| DE | 102010036186 A1 | 3/2012 |
| DE | 102010041763 A1 | 4/2012 |
| JP | 2005134311 A | 5/2005 |
| JP | 2007024508 A | 2/2007 |
| JP | 2007271441 A | 10/2007 |

OTHER PUBLICATIONS

Bugbee et al., "Absolute and Relative Gas Concentration: Understanding Oxygen in Air", Aug. 11, 2009, Apogee Instruments, pp. 1-10 <http://www.apogeeinstruments.com/content/AbsoluteandRelativeGasConcentration.pdf>.

Cavicchi, R. E., et al., "Fast Temperature Programmed Sensing for Micro-Hotplate Gas Sensors", IEEE, Electron Device Letters, vol. 16, No. 6, 1995, pp. 286-288.

Graunke, T. et al., "Effects on Implemented Pre-Heated Foamed Ceramic Filters", Elsevier, Proc. Eurosensors XXVI, Sep. 9-12, 2012, pp. 506-509.

Zudock, F., "Katalytisch aktive CuO-Membranen zur Selektivitaetssteuerung von Metalloxid-Gassensoren" FZKA 6220: 1998, 143 pgs.

* cited by examiner

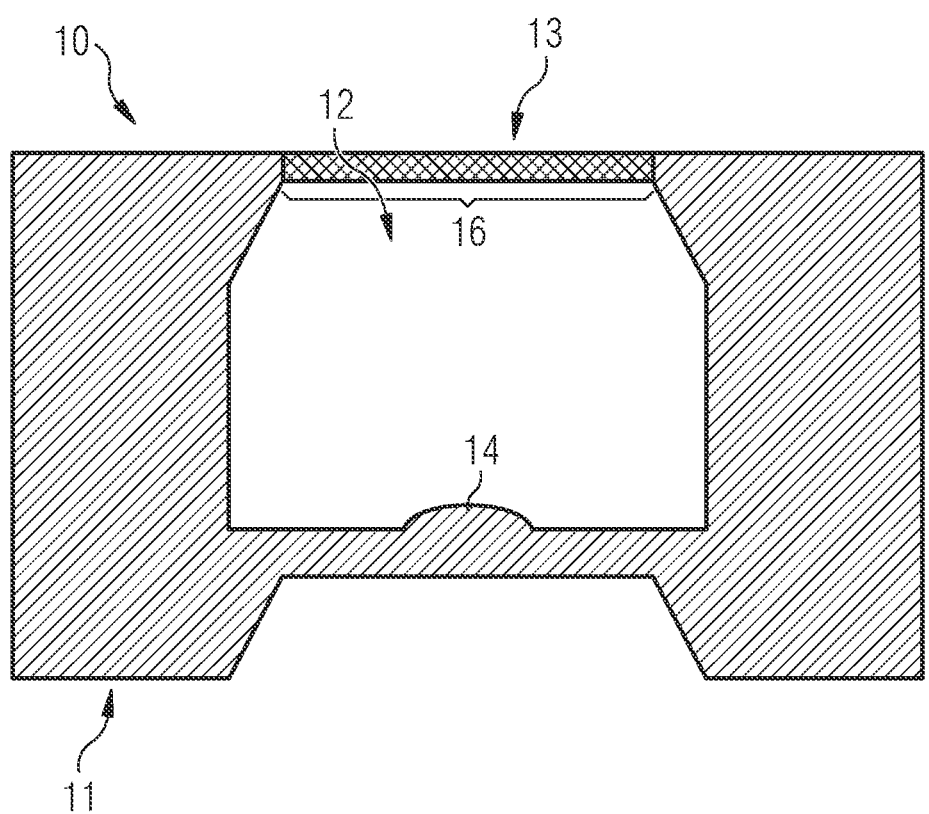

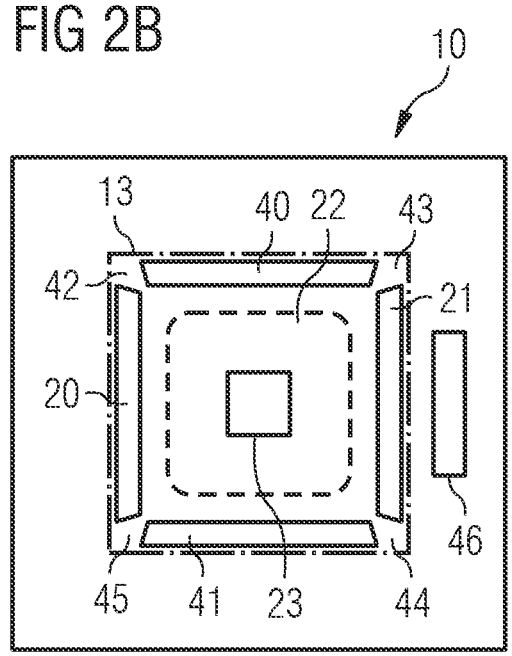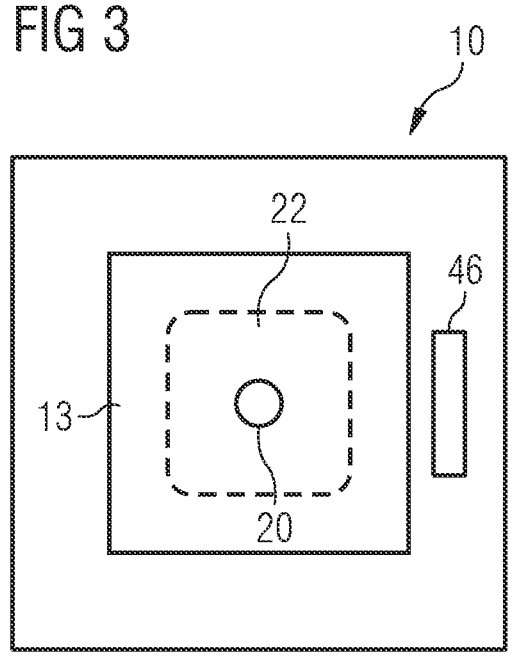

METHOD AND SENSOR SYSTEM FOR MEASURING GAS CONCENTRATIONS

CROSS-REFERENCE TO RELATED APPLICATION(S)

This application is a continuation of U.S. application Ser. No. 15/235,054, filed on Aug. 11, 2016, which is a continuation-in-part of International Application No. PCT/EP2015/052891, filed on Feb. 11, 2015, claiming the benefit of German Application No. 102014101657.2, filed on Feb. 11, 2014. The disclosures of the prior applications are incorporated herein by reference.

BACKGROUND OF THE INVENTION

The present patent application relates to a method and a sensor system for measuring the concentration of at least one gas from a gas sample.

Sensor systems for the detection of gases from a gas sample are already known in multifarious configurations. The accuracy of the concentration measurement of a gas in many sensors depends highly on the reactivity of the gas to be detected.

Furthermore, the determination of the concentration of a gas is influenced by the presence of other gases. A sensor signal originating from an individual gas can be lost in the noise of the sensor signals from competing gases, i.e. the sensor signal from the gas to be detected is hidden or is overlain by the sensor signals from the competing gases. Metal oxide sensors, for example for individual gases in specific temperature ranges, exhibit high signal strengths but, in the case of gas samples from a plurality of gases, exhibit superimposition of the signals. In this way, the selectivity of known sensor devices having such sensors is restricted.

SUMMARY OF THE INVENTION

In one embodiment, a method is configured to measure the concentration of at least one gas from a gas sample by using a sensor system which has a measuring area with at least one gas sensor, optionally a metal oxide sensor, the measuring area having a diffusion opening which is closed by a gas-permeable structure. The measuring area is initially heated up, the heating is then switched off and the change in resistance of the at least one gas sensor is measured.

By means of heating the measuring area, the gas concentration is reduced, given a constant pressure and volume in the measuring area. After the heating has been switched off, the concentration rises, which leads to a change in resistance in the at least one gas sensor. As a result, the concentration of the gases located in the measuring area can be measured. By means of the change in concentration produced artificially by means of diffusion, the sensitivity of the sensor system can be increased considerably.

As a result of the determination of the resistance of the gas sensor at two different concentrations of the gas in the measuring area, the accuracy of the measurement of the concentration of the gas in the space outside the sensor system is increased.

Alternatively, instead of switching off the heating, the heating power is reduced to a value different from 0. Both as a result of switching off the heating and also as a result of reducing the heating power, the temperature of the gas sample in the measuring area decreases as compared with the phase in which the measuring area is heated up. In order to determine the change in resistance of the gas sensor, at least one resistance value of the gas sensor is measured at a high temperature of the measuring area, and at least one resistance value of the gas sensor is measured at a low temperature of the measuring area.

In addition, the selectivity of the sensor system can also be increased. Apart from a selection of the sensitive layer of the at least one gas sensor which is matched to the target gas, the selectivity of the sensor system can be set by a sensor heating device for the at least one gas sensor and/or by the heating of the measuring area. The signal strengths from metal oxide sensors are different for different gases, given a constant concentration. The signal strengths can thus be changed via temperature modulation of the sensor heating device for the gas sensor and/or the heating of the measuring area.

The method can be used in an extremely wide range of different application areas. Thus, the gas sample can be an individual gas, a gas mixture and/or an aerosol.

The sensitivity and selectivity of the sensor system can additionally be increased for specific applications by the gas sample flowing and/or diffusing through at least one optionally heatable catalyst arrangement before it reaches the sensor system or the measuring area of the sensor system. The catalyst arrangement here can be integrated into the gas-permeable structure at the diffusion opening of the measuring area. The gases from the gas sample are at least partly converted by the catalyst arrangement into other gases, which are either easier to detect by the gas sensor or cannot be detected at all, and therefore do not influence the measured result, in order to obtain a more accurate measured result.

In one embodiment, a sensor system is configured to measure the concentration of at least one gas from a gas sample by using a measuring area in which at least one gas sensor, optionally a metal oxide sensor, is arranged and which has a diffusion opening which is closed by a gas-permeable structure. The measuring area is provided with a controllable heating device for the measuring area.

The sensor system can also be designated as a sensor device.

By using this sensor system, the method for determining the concentration of a gas can be carried out with high accuracy. By means of appropriate control of the heating device, the selectivity of the sensor arrangement can additionally be increased.

In one embodiment, the sensor system is configured such that the measuring area is initially heated up by the heating device and then the heating is switched off or the heating power is reduced to a value different from 0 watt. Furthermore, the sensor system can be configured such that a change in resistance of the at least one gas sensor is measured.

In one refinement of the sensor system, the structure closing the diffusion opening of the measuring area is heatable by the heating device.

In addition, the at least one gas sensor can also be heatable in order to be able to adapt the same optimally to the gas to be detected and thus to increase the selectivity of the sensor system.

The structure closing the diffusion opening of the measuring area can be a gas-permeable grid, a mesh, a porous solid body, a sponge or a membrane. Alternatively, a modulated radiant heater can be used as a heating device above the gas sensor, which can be suspended in the diffusion opening in such a way that the gas can flow past it.

The temperature of the gas sample in the measuring area can thus be modulated. By means of the modulation of the temperature of the gas sample, the concentration of the various gases in the gas sample is modulated.

In one embodiment, the concentration of a gas from the gas sample in the measuring area in a first phase during which the measuring area is heated up is different from the concentration of the gas from the gas sample in the measuring area in a second phase, during which the heating is switched off or the heating power is reduced to a value different from 0. In general, the concentration in the second phase is higher than in the first phase.

The measuring area can also be designated as a gas space, measuring chamber or sensor chamber. The measuring area is filled by the gas sample. The measuring area can be free of solid bodies.

In one embodiment, the gas-permeable structure and the at least one gas sensor are at a distance from each other. This free interspace is designated as a measuring area. The volume of the measuring area is produced by this space.

The diffusion opening is thus the inlet of the measuring area.

In one embodiment, exchange of the gas/the air in the measuring area with the gas/the air outside the sensor system takes place exclusively through the diffusion opening.

In one embodiment, the measuring area has a single diffusion opening.

In one embodiment, the measuring area has at least one diffusion opening. Exchange of the gas/the air in the measuring area with the gas/the air outside the sensor system takes place exclusively through the at least one diffusion opening.

In one embodiment, the sensor system is implemented as a microsystem, in English a micro-electro-mechanical system.

BRIEF DESCRIPTION OF THE DRAWINGS

Aspects of the invention will be explained in more detail below in a number of exemplary embodiments by using the Figures. Functionally and effectively identical components, layers or structures bear the same reference symbols. To the extent to which components, layers or structures correspond in terms of their function, the description thereof will not be repeated in each of the following Figures, in which:

FIG. 1 shows an exemplary embodiment of a sensor system,

FIGS. 2A and 2B show a further exemplary embodiment of the sensor system,

FIGS. 3 and 4 show further exemplary embodiments of the sensor system,

DETAILED DESCRIPTION

Figure 2A:
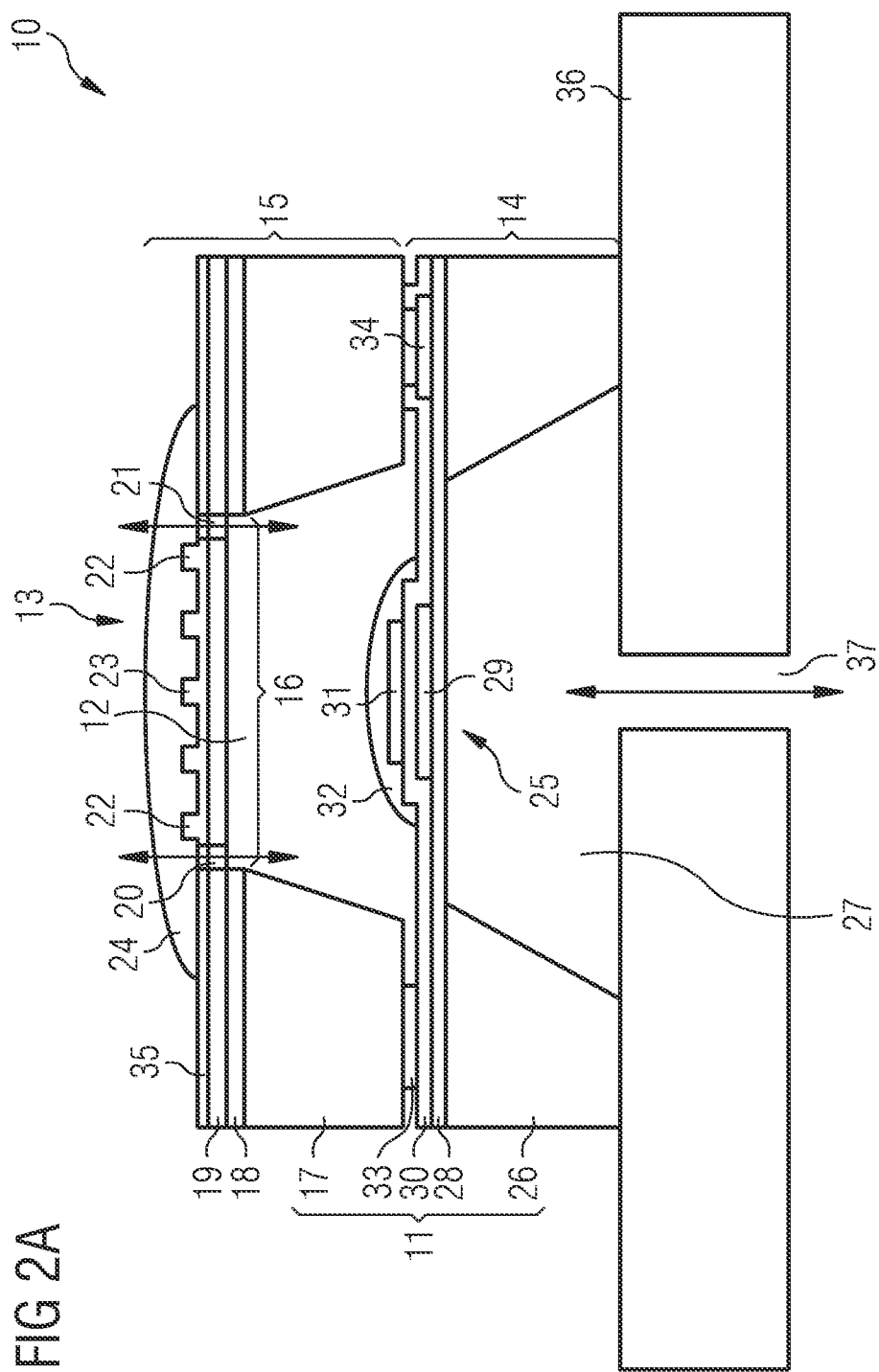

FIG. 1 shows an exemplary embodiment of a sensor system 10. An exemplary embodiment of the sensor system 10 will be explained in more detail below with reference to the drawing, which shows a cross section through the sensor system 10.

The sensor system 10 has a gas-tight housing 11, which encloses a measuring area 12. A diffusion opening 16 of the measuring area 12 is closed by a gas-permeable structure 13. Through the latter, gas from the surroundings can flow and/or diffuse into the measuring area 12 and to a gas sensor, a metal oxide sensor 14 here. In the example illustrated, the gas-permeable structure 13 is heatable by a heating device, not specifically illustrated, having a control device. If the gas-permeable structure 13 is heated up, then, as a result, the interior of the measuring area 12 is also heated, which leads to a reduction in the gas concentration in the measuring area 12. If the heating of the gas-permeable structure 13 is then stopped, more gas diffuses through the gas-permeable structure 13 into the measuring area 12 as a result of the cooling of the measuring area 12, which leads to a change in resistance of the metal oxide sensor 14. This change in resistance is registered by an evaluation device, not illustrated here. It is a measure of the gas concentration in the measuring area 12 and therefore also in the surroundings, as soon as the measuring area 12 and the surroundings have reached the same temperature. The metal oxide sensor 14 itself can also be heatable. As a result, it can be matched optimally to different gases. In addition, the selectivity of the sensor system 10 can be increased by mutually coordinated modulation of the temperature of the heating devices for the gas-permeable structure 13 and for the gas sensor 14.

The gas-permeable structure 13 can be a membrane, a porous solid body, a sponge or a grid. In addition, the gas-permeable structure 13 can also be made from a catalytically acting material. Furthermore, it is possible and expedient to arrange in the measuring area 12 a temperature sensor, not illustrated here, and possibly a humidity sensor, which is connected to the evaluation device for the sensor signals and the control device of the heating devices for the measuring area 12 and the gas sensor 14.

FIG. 2A shows a further exemplary embodiment of the sensor system 10 in cross section, which is a development of the embodiment shown in FIG. 1. The sensor system 10 comprises a measuring area semiconductor body 15, which has the diffusion opening 16. The measuring area semiconductor body 15 is implemented as a micromechanical component. The diffusion opening 16 is closed by the gas-permeable structure 13. The measuring area semiconductor body 15 is implemented as a silicon component. The measuring area semiconductor body 15 is produced from a silicon-on-insulator wafer, abbreviated SOI wafer. The gas-permeable structure 13 has an insulation layer 35. The insulation layer 35 can be made of silicon nitride, in particular $Si_3N_4$.

Furthermore, the gas-permeable structure 13 comprises a carrier layer 19. The carrier layer 19 can be a silicon layer, in particular made of monocrystalline silicon. The gas-permeable structure 13 is arranged on a frame 17 of the measuring area semiconductor body 15. An insulation layer 18 is located on the frame 17. The insulation layer 18 can be made of silicon oxide, in particular $SiO_2$. Here, the insulation layer 18 is arranged between the carrier layer 19 and the frame 17. The insulation layer 35 is arranged on the carrier layer 19. The measuring area 12 is primarily a recess in the measuring area semiconductor body 16, etched using micromechanical methods. The recess is realized as a cavity.

The layer structure, comprising the insulation layer 35 and the carrier layer 19, has at least one opening 20, 21. Gas can diffuse through the at least one opening 20, 21 from the exterior of the sensor system 10 into the measuring area 12. The two openings 20, 21 are implemented as through holes. Furthermore, the gas-permeable structure 13 has a heating device 22. The heating device 22 is implemented as a heating resistor. The heating device 22 is arranged on the insulation layer 35. The heating device 22 is integrated into the gas-permeable structure 13.

The gas-permeable structure 13 comprises a temperature sensor 23. The temperature sensor 23 can be formed as a temperature measuring resistor. The heating device 22 and the temperature sensor 23 can be produced from a thin metal film, in particular of platinum or nickel.

The temperature sensor 23 is arranged on the insulation layer 35 beside the heating device 22. The temperature sensor 23 is localized in the center of the gas-permeable structure 13. The heating device 22 is arranged around the temperature sensor 23. The measuring area semiconductor body 15 is thus implemented as an infrared radiator.

Furthermore, the gas-permeable structure 13 comprises a gas-permeable covering layer 24. The gas-permeable covering layer 24 covers the at least one opening 20, 21 in the layer structure comprising the insulation layer 35 and the carrier layer 19. The gas-permeable covering layer 24 can be porous. The gas-permeable covering layer 24 can be implemented as a sintered layer. For example, the gas-permeable covering layer 24 can be produced as sintered ceramic. The ceramic can, for example, primarily have aluminum oxide, tin oxide or silicon carbide, in particular $Al_2O_3$ or $SnO_2$ or SiC.

The gas-permeable covering layer 24 can also be implemented as a catalyst layer or catalyst arrangement. To this end, it has, for example, palladium and/or platinum and/or gold as material. The sintered ceramic layer can thus have proportions of palladium and/or platinum and/or gold in addition to the basic material such as aluminum oxide, tin oxide or silicon carbide. The gas-permeable structure 13 can thus also comprise the catalyst arrangement.

The gas-permeable structure 13 thus has a gas-permeable grid and a porous solid body. The gas-permeable grid is formed by the layer structure, which comprises the insulation layer 35 and the carrier layer 19, and the at least one opening 20, 21 in the layer structure. The porous solid body can be implemented by the gas-permeable covering layer 24.

Furthermore, the sensor system 10 comprises the gas sensor 14. The gas sensor 14 is implemented as a metal oxide sensor, also called a metal-oxide-semiconductor gas-sensor. The gas sensor 14 is implemented as a micromechanical component. The gas sensor 14 comprises a sensor frame 26. The gas sensor 14 has a sensor membrane 25. The sensor membrane 25 spans a recess 27 in the gas sensor 14. The recess 27 is located between the sensor frame 26. The recess 27 is etched using micromechanical methods. The sensor membrane 25 is not gas-permeable. The sensor membrane 25 has a first insulation layer 28. The first insulation layer 28 can be produced as a silicon nitride layer, in particular a $Si_3N_4$ layer. On the first insulation layer 28, a sensor heating device 29 of the gas sensor 14 is arranged over the recess 27. A second insulation layer 30 is arranged on the sensor heating device 29. The second insulation layer 30 can be deposited as a silicon nitride layer, in particular a $Si_3N_4$ layer.

The gas sensor 14 comprises an electrode assembly 31. Furthermore, the gas sensor 14 has a sensitive layer 32. The electrode assembly 31 is located on the second insulation layer 30. The electrode assembly 31 can be implemented as an interdigital electrode assembly. The sensitive layer 32 is deposited on the electrode assembly 31. If the gas sensor 14 is implemented as a metal oxide sensor, then the sensitive layer 32 is a metal oxide. The metal oxide can be, for example, tin oxide, zinc oxide, gallium oxide or tungsten oxide, in particular $SnO_2$, $ZnO$, $Ga_2O_3$ or $WO_3$. The metal oxide can be impregnated with a noble metal, such as palladium or platinum.

The metal oxide can be produced as a ceramic. The ceramic can be sintered and consist of tin oxide, zinc oxide, gallium oxide or tungsten oxide. The gas sensor 14 can thus be implemented as a thick layer sensor. The sensitive layer 32 is a porous layer. The layer thickness of the sensitive layer 32 lies typically in the micrometer range.

The sensitive layer 32 can be applied, for example, by means of a droplet technique, aerosol technique, plunger technique or screen-printing methods. In the droplet technique, a droplet of the starting material of the sensitive layer 32 is discharged onto the electrode assembly 31. The droplet is applied by means of a needle. In the aerosol technique, an aerosol is produced from the starting material, for example by evaporation. The aerosol is deposited on the base—such as the electrode assembly 31 and the second insulation layer 30; in this case the layer thickness of the sensitive layer 32 can be set by means of an opening time of a shutter. In the plunger technique, with the aid of a plunger or punch, the starting material is picked up and applied to the electrode assembly 31. In these different methods, the starting material is tempered or subjected to an annealing process, so that the sensitive layer 32 formed as a ceramic is produced.

Alternatively, the gas sensor 14 can be implemented as a thin film sensor. The sensitive layer 32 is a compact layer. The layer thickness of the sensitive layer 32 typically lies in the nanometer range. A thin sensitive layer 32, for example of tin oxide, zinc oxide, gallium oxide or tungsten oxide, can be produced by sputtering or vapor deposition.

The frame 26 and the sensor frame 17 form the housing 11 of the sensor system 10. The measuring area semiconductor body 15 and the gas sensor 14 are connected to each other via a suitable connecting technique. For this purpose, a connecting layer 33 can be arranged between the gas sensor 14 and the measuring area semiconductor body 15. The connection is merely indicated in FIG. 2A. For the connection, for example, a temperature-resistant adhesive such as a cement adhesive, a solder, a eutectic compound, silicon fusion bonding or an anodic connection can be used. Furthermore, the gas sensor 14 has at least one contact surface 34, also called a bond pad. An electrically conductive connection to the bond pad 34 from outside can be implemented, for example, before the measuring area semiconductor body 15 is placed on the gas sensor 14.

The measuring area semiconductor body 15 and the gas sensor 14 are stable and permanently connected to each other. The measuring area 12 is a chamber or cavity formed between the measuring area semiconductor body 15 and the gas sensor 14.

Furthermore, the sensor system 10 has a carrier 36. The carrier 36 can be implemented as a ceramic carrier, as a printed circuit board or as a header. For example, the header can be a transistor outline header, abbreviated TO header. The carrier 36 has a carrier opening 37 which leads to the recess 27. Air/gas from the recess 27 can flow out through the carrier opening 37. Thus, the carrier opening 37 in the carrier 36 prevents an overpressure from being produced in the recess 27, which, for example, can lead to the destruction of the sensor membrane 25. The carrier opening 37 can be implemented as a drilled hole. The carrier opening 37 is used for pressure equalization between the recess 27 and the surroundings. The sensor frame 26 is connected to the carrier 36 by a connecting technique not shown.

The sensor heating device 29 is fed with electrical energy via two bond pads 34. The sensor heating device 29 heats the sensor membrane 25 and therefore the sensitive layer 32. The change in resistance in the sensitive layer 32 is measured by means of the electrode assembly 31. A sensor signal S3 can be tapped off at two further bond pads. From a total of four bond pads, the bond pad 34 is shown by way of example.

The heating device 22 heats up the layer structure, comprising the insulation layer 35 and the carrier layer 19, and also the gas-permeable covering layer 24. Thus, the volume of the measuring area 12 is heated up. In the process, the air or the gas which is located in the measuring area 12 is heated up by the heating device 22. The temperature sensor 23 is used to measure the temperature of the gas-permeable structure 13. The measuring area 12 is primarily implemented by the recess in the frame 17. The measuring area 12 is the space enclosed by the sensor membrane 25, the frame 17 and the gas-permeable structure 13. The heating device 22 and the sensor heating device 29 lead to heating of the air/the gas in the measuring area 12. An overpressure produced by the heating is dissipated through the at least one opening 20, 21. The concentration of a gas is the number of molecules of the gas per unit volume. The concentration of the gas decreases as a result of the heating of the measuring area 12.

As a result of switching off the heating device 22, for example, the temperature of the air/the gas in the measuring area 12 decreases, so that gas/air diffuses into the measuring area 12 through the gas-permeable covering layer 24. The concentration of the gas thus increases as the temperature falls.

As a result of catalytically acting constituents of the gas-permeable covering layer 24, the air/gas flowing into the measuring area 12 is changed as compared with the air/gas which is located outside the sensor system 10. By means of the catalytically acting constituents of the gas-permeable covering layer 24, for example, carbon monoxide can be converted into carbon dioxide. Depending on the catalyst material used and depending on the gas to be detected, different temperatures are set in the gas-permeable structure 13. In one example, the temperature in the gas-permeable structure can be 350 to 400° C.

In an embodiment, a value of the temperature is reached inside the measuring area 12 and/or at the diffusion opening 16 that at least one gas of the gas sample is burnt or oxidized. The value of the temperature may be between 100 to 650° C. Thus, in a first phase A that will be explained below, at least one gas of the gas sample will be burnt and thus does not diffuse to the gas sensor 14. For example, an alcohol such as ethanol is burnt into water and carbon dioxide. The gas sensor 14 measures no concentration or only a small concentration of the at least one gas. In a second phase B that will be explained below the temperature inside the measuring area 12 and/or at the diffusion opening 16 is reduced, and the at least one gas of the gas sample is not burnt or oxidized and is able to diffuse to the gas sensor 14. Therefore, the gas sensor 14 reacts on a high difference in concentration of the at least one gas of the gas sample.

For example, in the first phase A, the temperature may be between 100 to 300° C. The sensor system 10 may be configured to detect an aldehyde such as formaldehyde or acetaldehyde or a sulfur compound.

In the second phase B, the temperature is lower than in the first phase A.

Alternatively, in the first phase A, the temperature may be between 300 to 650° C. The sensor system 10 may be configured to detect ozone, hydrogen, ethanol, acetone, methane or carbon monoxide. In the second phase B, the temperature may be between room temperature and 250° C.

At lower temperatures, the number of different gases that can be burnt is smaller than at higher temperatures. By selecting the temperature achieved in the first phase A in the measuring area 12, the gas or gases to be burnt can be selected. Thus, the selectivity of the sensor system 10 can be changed by selecting the temperature of the measuring area 12 in the first phase A. Optionally, the gas-permeable structure 13 may be free of a catalytically active constituent.

In an alternative embodiment, not shown, the heating device 22 is used simultaneously as a temperature sensor as well. Here, the temperature sensor 23 can be left out.

In an alternative embodiment, not shown, the gas-permeable covering layer 24 has no catalytically active constituents.

In an alternative embodiment, not shown, the gas-permeable covering layer 24 can be omitted. Since the dimensions of the openings 20, 21 are kept very small, the gas exchange of the measuring area 12 with the space outside the sensor system 10 takes place exclusively by diffusion.

In an alternative embodiment, not shown, the carrier layer 19 can be omitted. The gas-permeable structure 13 is therefore free of monocrystalline silicon.

In alternative embodiment, not shown, the gas sensor 14 is implemented as a thermal catalytic sensor. A thermal catalytic sensor has no sensor electrodes 31. If the gas sensor 14 is implemented as a thermal catalytic sensor, it has the sensor frame 26, the sensor membrane 25, the sensor heating device 29 and the sensitive layer 32. The sensitive layer 32 is implemented as a catalytically active layer. The catalytically active layer has, for example, a noble metal such as platinum or palladium, or metal oxides such as manganese oxide or copper(II) oxide. If gas in the measuring area 12 is converted on the sensitive layer 32, the reaction leads to an increase in the temperature of the sensor membrane 25. The temperature increase can be determined by means of an additional temperature sensor or by means of determining the resistance of the sensor heating device 29.

In an alternative embodiment, not shown, the gas sensor 14 is implemented as a thermal conductivity sensor. Here, the gas sensor 14 measures the thermal conductivity between the sensor membrane 25 and the gas-permeable structure 13. If gas with a high thermal conductivity flows into the measuring area 12, then the thermal conduction between a hot surface and a cold surface increases. For example, the heating device 22 can be switched on and the sensor heating device 29 can be switched off. Thus, the heating of the sensor membrane 25 is measured by a thermally conductive gas with the gas-permeable structure 13 as heat source. The rise in the temperature of the sensor membrane 25 is higher, the more thermally conductive the gas in the measuring area 12 is.

Alternatively, the change in temperature of the gas-permeable structure 13 is measured. Given a constant heating power from the heating device 22, the temperature of the gas-permeable structure 13 in the case of a less thermally conductive gas in the measuring area 12 increases more than in the case of a more highly thermally conductive gas.

Alternatively, the sensor membrane 25 is heated up by means of the sensor heating device 29, the heating device 22 is deactivated and the transfer of heat from the sensor membrane 25 to the gas-permeable structure 13 is measured. Here, too, either the change in the temperature of the sensor membrane 25 or that of the gas-permeable structure 13 can be measured.

The gas sensor 14 can thus be implemented as a chemical gas sensor—such as a metal oxide sensor—as a chemical/physical gas sensor—such as a thermal catalytic sensor—or as a physical gas sensor—such as a thermal conductivity sensor. Alternatively, the gas sensor 14 can be implemented as a humidity sensor.

FIG. 2B shows a plan view of an exemplary embodiment of the sensor system 10, which is a development of the embodiments of the sensor system 10 shown in FIGS. 1 and 2A. The gas-permeable structure 13 is implemented as a gas-permeable grid and, in addition to the openings 20, 21 shown in cross section in FIG. 2A, has two further openings 40, 41. The openings 20, 21, 40, 41 are implemented approximately as rectangles or elongated slots. The openings 20, 21, 40, 41 are arranged approximately on an inner edge of the frame 17. Only narrow webs 42 to 45 connect the frame 17 with an inner area of the gas-permeable structure 13. The gas-permeable structure 13 can thus have exactly four openings 20, 21, 40, 41. The center of the gas-permeable structure 13 is heated. Thus, thermal dissipation and therefore the energy consumption are kept low. Furthermore, the measuring area semiconductor body 15 has a further temperature sensor 46. The further temperature sensor 46 is arranged on the frame 17 here. The further temperature sensor 46 can be provided in addition to or instead of the temperature sensor 23 arranged on the gas-permeable structure 13.

In an alternative embodiment, not shown, the measuring area semiconductor body 15 is free of the heating device 22. The measuring area 12 is only heated by the sensor heating device 29. Thus, the heating of the space outside of the sensor system 10 is reduced.

In an alternative embodiment, not shown, the measuring area semiconductor body 15 is free of the temperature sensor 23.

In an alternative embodiment, not shown, the measuring area semiconductor body 15 is free of the heating device 22 and of the temperature sensor 23. Thus, the measuring area semiconductor body 15 is realized as a passive element and does not comprises any bond pad or another electrical contact. The measuring area semiconductor body 15 can be fabricated at low cost.

FIG. 3 shows a further exemplary embodiment of a plan view of the sensor system 10, which is a development of the embodiment shown in FIGS. 1, 2A and 2B. Here, the gas-permeable structure 13 has the opening 20. The gas-permeable structure 13 is implemented as a thin membrane, so that the heating power is advantageously kept low. The number of openings 20 of the gas-permeable structure 13 can be exactly one. The opening 20 is implemented in the form of a circle. The opening 20 is located approximately in the center of the gas-permeable structure 13. The opening 20 is thus located approximately in the center of the frame 17.

Alternatively, the gas-permeable structure 13 can have additional openings. The additional openings can likewise be implemented in the form of circles. The additional openings can be arranged regularly on the gas-permeable structure 13. The gas-permeable structure 13 is implemented as a membrane, which closes the diffusion opening 16. By means of the choice of the number of openings 20 and the size of the openings 20, the level of the diffusion between an outer gas space and the measuring area 12 can be set. The same level of diffusion can be achieved by a large opening 20 and several small openings. Thus, the number of openings 20 may one, two, three, four or more than four.

Figure 4:
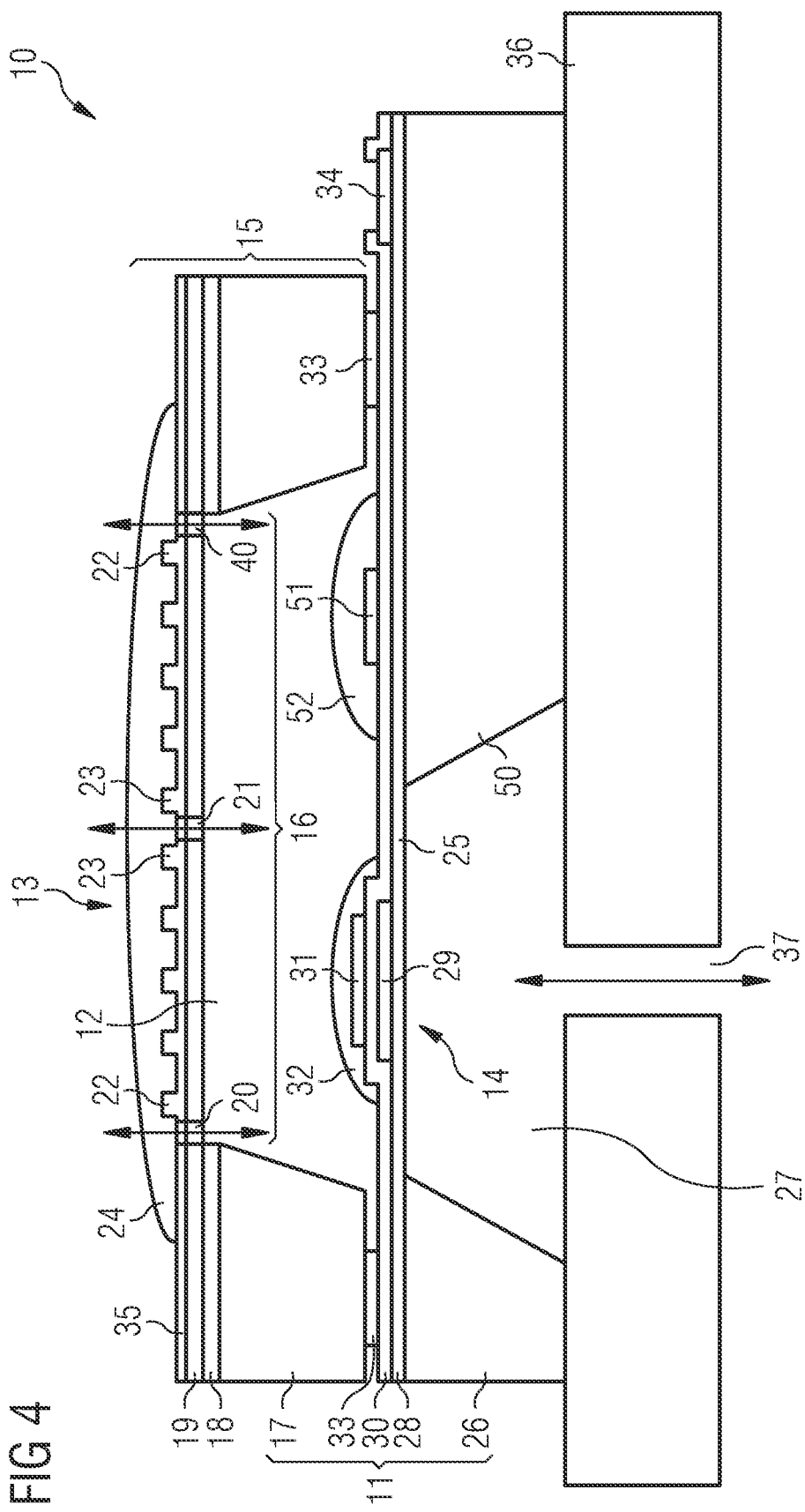

FIG. 4 shows a further exemplary embodiment of the sensor system 10, which is a development of the embodiments shown in FIGS. 1, 2A, 2B and 3. The sensor system 10 comprises at least one further sensor 50. The further sensor 50 and the gas sensor 14 are integrated on a semiconductor body. The further sensor 50 can be, for example, a further gas sensor or a humidity sensor. The further sensor 50 can be arranged on the sensor frame 26. The further sensor 50 comprises a further electrode assembly 51 and a further sensitive layer 52. In the case of a humidity sensor, the further sensitive layer 52 is a moisture-absorbing dielectric. The further electrode assembly 51 detects changes in the moisture-sensitive dielectric. The further electrode assembly 51 is arranged on the first insulation layer 28. The gas/the air in the measuring area 12 is thus in contact with the gas sensor 14 and the further sensor 50. The further sensor 50 thus detects a further parameter in the measuring area 12.

The measuring area semiconductor body 12 is implemented in such a way that contact can be made with the at least one bond pad 34 from outside. A width of the measuring area semiconductor body 12 is thus smaller than a width of the semiconductor body which comprises the gas sensor 14.

In an alternative embodiment, not shown, the further sensor 50 is implemented in a way corresponding to the gas sensor 14. Thus, the further sensor 50 comprises a further sensor membrane and a further recess.

Figure 5:
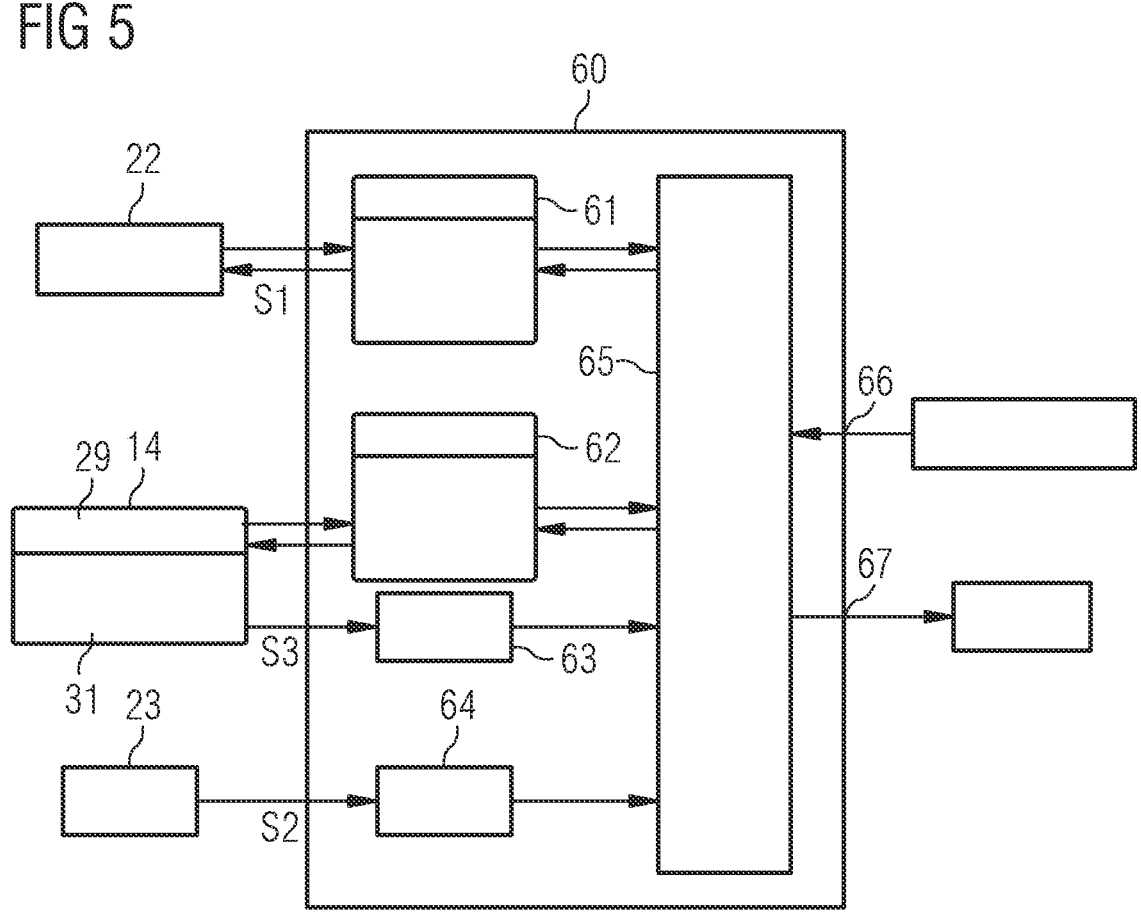
FIG. 5 shows an exemplary embodiment of a circuit diagram of the sensor system.

FIG. 5 shows an exemplary embodiment of an electric circuit diagram of the sensor system 10. The sensor system 10 comprises an evaluation device 60. The gas sensor 14, the heating device 22 and the temperature sensor 23 are connected to the evaluation device 60. The evaluation device 60 has a control device 61, which supplies the heating device 22 with electrical energy in the form of heating power S1. The heating device 22 is controllable by means of the control device 61. The heating device 22 can be implemented as a resistor. The resistor is temperature-dependent.

The temperature sensor 23 provides a temperature sensor signal S2. The temperature sensor signal S2 can, for example, depend on a resistance value of the temperature sensor 23.

The control device 61 can have different control mechanisms. The control device 61 can be designed to initially switch on and then switch off the heating device 22.

For example, the control device 61 can provide a heating power S1 with a constant value SC from the heating device 22 in a first phase A.

In an alternative embodiment, the control device 61 can be designed to set a first constant temperature of the measuring area 12 in the first phase A. Here, the control device 61 can provide a heating power S1 from the heating device 22 such that a resistance value of the heating device 22 is constant. It is thus possible for a constant temperature value of the measuring area 12 to be set via the control device 61. The temperature value can be determined by means of the temperature sensor 23. The control device 61 can be designed to set a second constant temperature of the measuring area 12 above room temperature in a second phase B, or to set the heating power S1 to 0 watt and thus to switch off the heating in the second phase B.

The control device 61 can provide the heating power S1 in a pulse-width modulated manner.

Alternatively, the control device 61 can be implemented in such a way that it carries out power modulation. For example, the control device 61 can continuously increase and/or likewise continuously reduce the heating power S1 which the heating device 22 provides.

Thus, the heating power S1 may have a profile such as a saw tooth profile, a triangular form, a staircase form, a sinus form or a half sinus form. Consequently, the temperature of the measuring area 12 may also have a profile such as a saw tooth profile, a triangular form, a staircase form, a sinus form or a half sinus form. The gas sensor 14 may perform measurements at two, three, four or more than four points of time of a period. The profile of the heating power S1 may be periodically repeated. Thus, the gas sensor 14 may perform measurements at two, three, four or more than four different temperatures. For example, the gas sensor 14 performs measurements at the lowest and at the highest temperature and at least one temperature between the highest and the lowest temperature.

The evaluation device 60 comprises a sensor control device 62, which is coupled to the gas sensor 14. The sensor heating device 29 is connected to the sensor control device 62. The sensor control device 62 can be implemented in accordance with one of the variants outlined above for the control device 61. Here, a constant temperature value of the sensor membrane 25 can be set by the sensor control device 62. The heating device 22 and the sensor heating device 29 can, for example, be set independently of each other.

The gas sensor 14 provides a sensor signal S3. The sensor signal S3 can be formed, for example, as a current signal, a constant voltage being applied to the electrode assembly 31. Alternatively, the sensor signal S3 can be formed as a voltage, a constant current flowing through the sensitive layer 32 via the electrode assembly 31. The sensor signal S3 can thus represent a resistance value of the sensitive layer 32.

The evaluation device comprises a microcontroller 65, which is coupled to the gas sensor 14, the heating device 22 and the temperature sensor 23. Here, the control device 61 connects the microcontroller 65 to the heating device 22. In a corresponding way, the sensor control device 62 couples the microcontroller 65 to the gas sensor 14. A sensor filter 63 couples the gas sensor 14 and the microcontroller 65. A temperature sensor filter 64 is arranged between the temperature sensor 23 and the microcontroller 65. The microcontroller 65 can comprise at least one analog-digital converter for digitizing the temperature sensor signal S2 and/or the sensor signal S3. The control device 61 and/or the sensor control device 62 can also be implemented in the microcontroller 65.

Data is fed to the microcontroller 65 via an input 66. The data can be, for example, commands such as switch on and switch off or calibration data. The microcontroller 65 also has at least one output 67. The output 67 can be implemented as a digital output and/or as an analog output. The microcontroller 65 carries out a calculation by using the sensor signal S3 from the gas sensor 14. The microcontroller 65 is designed to drive the heating device 22 and the sensor heating device 29 and also to evaluate the sensor signal S3 and the temperature signal S2. The microcontroller 65 can, for example, provide the digitized sensor signal S3 on its output 67.

Alternatively, the microcontroller 65 can provide on its output 67 information about a gas concentration, which is determined by means of the sensor signal S3. For this purpose, the microcontroller 61 evaluates values of the sensor signal S3 which have been determined during or at the end of a heating phase, and also values of the sensor signal S3 which have been determined after the heating has been switched off or the heating power S1 has been reduced to a value different from 0 watt. Alternatively, instead of the microcontroller 65, a microprocessor can be provided.

Figure 6:
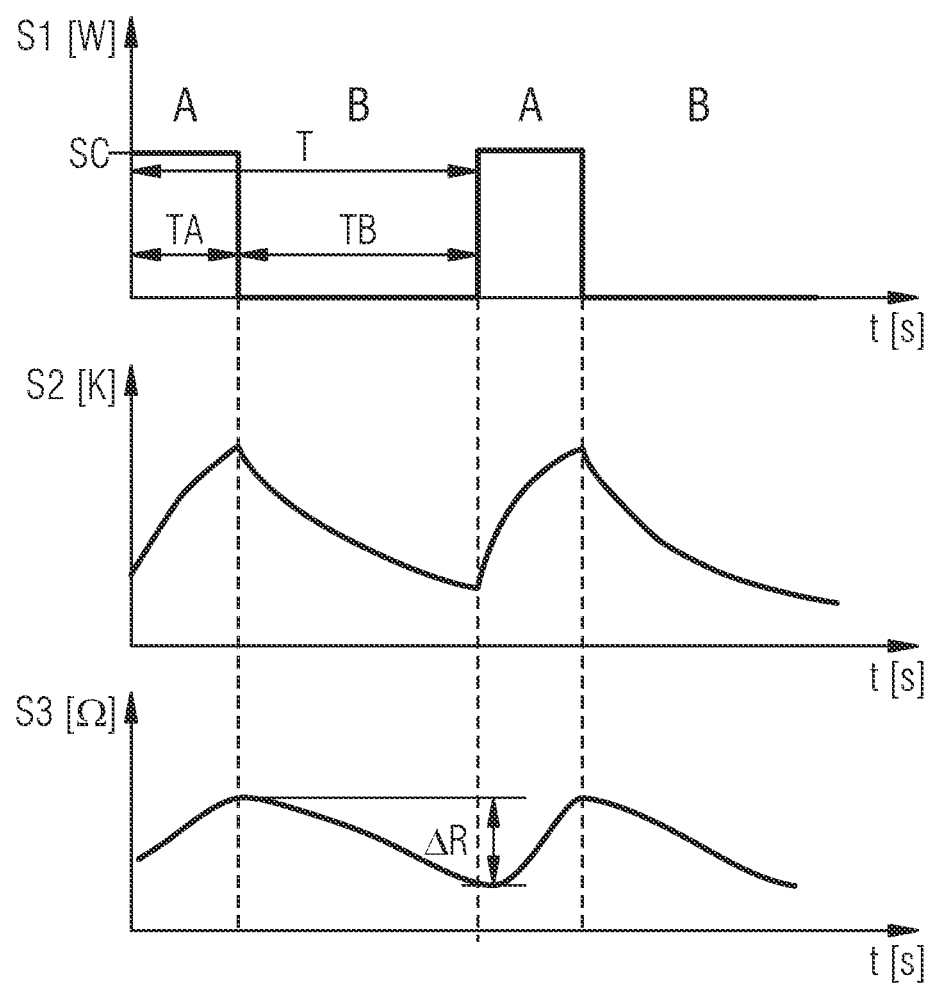
FIG. 6 shows an exemplary embodiment of the signals in the sensor system.

FIG. 6 shows an exemplary embodiment of the signals in the sensor signal 10. The heating power S1, the temperature sensor signal S2 and the sensor signal S3 are plotted against the time t. One period is composed of the first and the second phase A, B. While, in the first phase A, the heating power S1 assumes the value SC, the heating power S1 in the second phase B has the value 0. A period length T of the period is thus the sum of a first length TA of the first phase A and a second length TB of the second phase B. The first phase A and the second phase B alternate. The period length T can be constant. The temperature sensor signal S2 rises in the first phase A and falls in the second phase B. The second length TB of the second phase B can be chosen to be so short that the temperature sensor signal S2 does not fall to the value at room temperature.

According to the general gas equation:

$$p \cdot V = n \cdot R_m \cdot T,$$

where p is the pressure in the measuring area 12, V is the volume of the measuring area 12, n is the quantity of the substance of all the gases in the measuring area 12, $R_m$ is the general gas constant, and T is the absolute temperature in the measuring area 12. The pressure p and the volume V of the measuring area 12 are approximately constant. Therefore, the quantity of substance and therefore the particle count of all the gases and therefore the concentration of a gas is proportional to the reciprocal 1/T of the absolute temperature. With a high temperature in the measuring area 12, the concentration of the molecules is thus lower than with a low temperature in the measuring area 12. The following equation results from the above equation:

$$n_2 = n_1 \cdot T_1 / T_2,$$

where $n_2$ is the quantity of substance in the measuring area 12 at the temperature $T_2$ in the measuring area 12, and $n_1$ is the quantity of substance in the measuring area 12 at the temperature $T_1$ in the measuring area 12.

The measuring area 12 has the temperature $T_1$ in the first phase A and the temperature $T_2$ in the second phase B. For example, the temperature $T_1$ may be in the range of 423 to 473 kelvin corresponding to 150 to 200° C. The temperature $T_2$ is lower than the temperature $T_1$. The difference may be for example: $T_1 - T_2 \geq 100$ kelvin or, alternatively, $T_1 - T_2 \geq 50$ kelvin. The temperature $T_2$ may be e.g. in the range between room temperature and 373 kelvin corresponding to 100° C.

The values for the first length TA, the second length TB and the heating power S1 in the first phase A are chosen in such a way that a change in concentration of the gas in the measuring area 12 is produced. Switching off the heating device 22 at the change from the first phase A to the second phase B thus leads to an increase in the concentration of the gas.

The sensor signal S3 depends on the concentration of the gas to which the sensitive layer 32 is sensitive, and therefore depends on the temperature sensor signal S2. The sensor signal S3 can be the resistance value of the gas sensor 14. In the case of a sensitive layer 32 of $SnO_2$, the increase, for example of a carbon monoxide concentration in the measuring area 12, leads to a reduction in the sensor signal S3. The result is therefore a change in resistance $\Delta R$. In order to determine the concentration of the gas, at least one value of the sensor signal S3 is measured in the first phase A, and at least one value of the sensor signal S3 is measured in the second phase B. The concentration of the gas can be determined from the values of the sensor signal S3 determined in this way. The concentration of the gas determined by the sensor system 10 is a function of the at least one value of the sensor signal S3 in the first phase A and of the at least one value of the sensor signal S3 in the second phase B. For example, the concentration determined by the sensor system 10 can be a function of the difference ΔR of the values of the sensor signal S3.

The temperature of the gas sensor 14 is kept approximately constant in a period. In order to increase the selectivity, the temperature of the gas sensor 14 can be set differently in successive periods.

In an alternative embodiment, not shown, a signal profile has more than two phases. The more than two phases have different heating powers.

Alternatively, the heating power S1 has a value greater than 0 watt during the second phase B.

Figure 7:
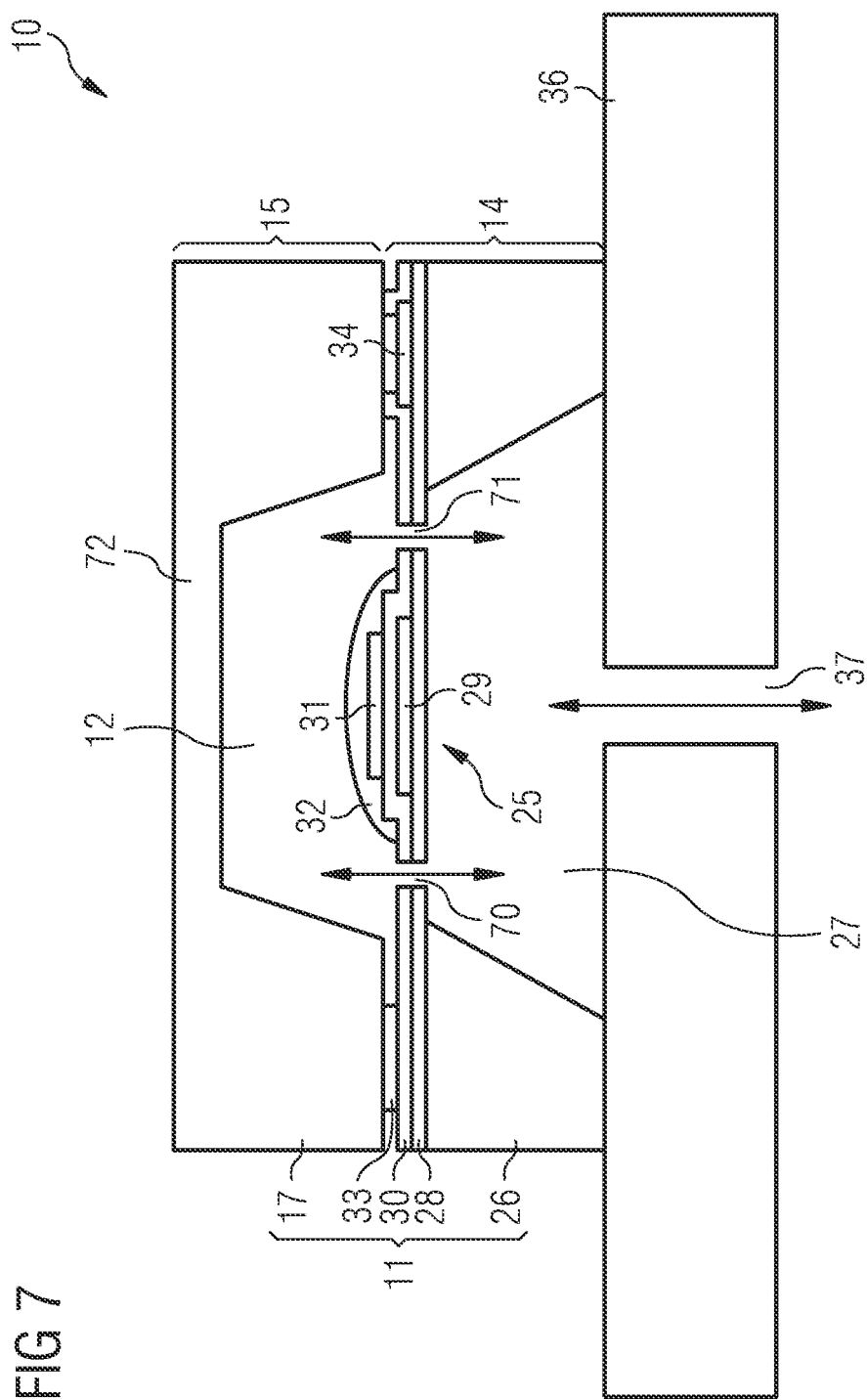
FIG. 7 shows a further exemplary embodiment of the sensor system.

FIG. 7 shows a further exemplary embodiment of the sensor system 10, which is a further development of the above shown embodiments. The gas sensor 14 comprises at least one opening 70, 71. The sensor membrane 25 comprises the at least one opening 70, 71. Thus, gas can diffuse through the at least one opening 70, 71 from one side of the sensor membrane 25 to the other side. The gas sensor 14, especially the sensitive layer 32, is directed towards the measuring area semiconductor body 15.

The measuring area semiconductor body 15 is free of the diffusion opening 16, the gas-permeable structure 13 and the at least one opening 20. The measuring area semiconductor body 15 is realized as a cap. The frame 17 of the measuring area semiconductor body 15 is closed by a tight membrane 72. The tight membrane 72 may comprise a silicon layer. Thus, the tight membrane 72 and the frame 17 are fabricated from the same semiconductor substrate. Alternatively, the tight membrane 72 is realized by an isolator layer arranged on the frame 17. The isolator layer may comprise silicon nitride or silicon oxide.

The at least one gas of the gas sample may flow or diffuse through the carrier opening 37, the recess 27 and the at least one opening 70, 71 of the gas sensor 14 to the measuring area 12. The at least one opening 70, 71 of the gas sensor 14 takes over the function of the diffusion opening 16 shown in FIGS. 1 to 4. The gas-permeable structure 13 of the diffusion opening 16 of the measuring area 12 is realized by the at least one opening 70, 71 of the gas sensor 14.

The measuring area semiconductor body 15 may be free of the heating device 22 and of the temperature sensor 23.

The sensor heating device 29 may be configured to provide heat to the measuring area 12. The gas sensor 14 is realized as a micro hot plate. A gap between the sensor membrane 25 and the measuring area semiconductor body 15 may be between 20 µm to 400 µm, optionally between 50 µm to 150 µm. Since the measuring area semiconductor body 15 and the gas sensor 14 are both realized using silicon as substrate, the thermal expansion coefficients match and the sensor system 10 has a high stability and long lifetime.

In an alternative embodiment, the measuring area semiconductor body 15 is replaced by a cap that is fabricated from other materials such as glass, quartz or ceramics. The cap may be flat or may have a cavity or recess similar to the measuring area semiconductor body 15. The connecting layer 33 may have a high thickness to achieve the gap between the sensor membrane 25 and the cap.

I claim:

1. A sensor system for measuring a concentration of at least one gas from a gas sample, the sensor system comprising:
    a carrier implemented as one of a ceramic carrier, a printed circuit board or a transistor outline header;
    a measuring area semiconductor body implemented as a first micromechanical component;
    a gas sensor implemented as a second micromechanical component and comprising an electrode assembly, a sensitive layer and a sensor membrane that spans a recess, wherein the measuring area semiconductor body and the gas sensor are connected to each other;
    a further sensor with a further electrode assembly and a further sensitive layer, wherein the further sensor is a further gas sensor or a humidity sensor; and
    a measuring area filled by the gas sample and arranged between the measuring area semiconductor body and the gas sensor, wherein the gas in the measuring area is in contact with the gas sensor and the further sensor,
    wherein the carrier has a carrier opening leading to the recess of the gas sensor,
    wherein the carrier opening is configured to equalize pressure between the recess and surroundings of the sensor system, and
    wherein the sensor system is operable to:
        initially heat up the measuring area by a heating device, and then switch off a heating or reduce a heating power to a value different from 0, and
        measure a change in resistance of the gas sensor.

2. The sensor system of claim 1, wherein the measuring area semiconductor body has a diffusion opening.

3. The sensor system of claim 1, wherein the further sensor and the gas sensor are integrated on a semiconductor body.

4. The sensor system of claim 1, wherein the gas sensor comprises a sensor frame, wherein the recess is located in the sensor frame, and wherein the further sensor is arranged on the sensor frame.

5. The sensor system of claim 1, wherein the further sensor comprises a further sensor membrane.

6. The sensor system of claim 5, wherein the further sensor additionally comprises a further recess.

7. The sensor system of claim 1, wherein the gas sensor is implemented as a metal oxide sensor.

8. The sensor system of claim 1, wherein the measuring area semiconductor body is implemented as a silicon component.

9. A sensor system for measuring a concentration of at least one gas from a gas sample, the sensor system comprising:
    a carrier implemented as one of a ceramic carrier, a printed circuit board or a transistor outline header;
    a measuring area semiconductor body implemented as a first micromechanical component;
    a gas sensor implemented as a second micromechanical component and comprising an electrode assembly, a sensitive layer and a sensor membrane that spans a recess, wherein the measuring area semiconductor body and the gas sensor are connected to each other;
    a humidity sensor with a further electrode assembly and a further sensitive layer; and
    a measuring area filled by the gas sample and arranged between the measuring area semiconductor body and the gas sensor, wherein the gas sample in the measuring area is in contact with the gas sensor and the humidity sensor,
    wherein the carrier has a carrier opening leading to the recess of the gas sensor,
    wherein the carrier opening is configured to equalize pressure between the recess and surroundings of the sensor system, and
    wherein the sensor system is operable to:

initially heat up the measuring area by a heating device, and then switch off a heating or reduce a heating power to a value different from 0, and measure a change in resistance of the gas sensor.

10. The sensor system of claim 9, wherein the measuring area semiconductor body has a diffusion opening.

11. The sensor system of claim 9, wherein the humidity sensor and the gas sensor are integrated on a semiconductor body.

12. The sensor system of claim 9, wherein the gas sensor comprises a sensor frame, wherein the recess is located in the sensor frame, and wherein the humidity sensor is arranged on the sensor frame.

13. The sensor system of claim 9, wherein the humidity sensor comprises a further sensor membrane.

14. The sensor system of claim 13, wherein the humidity sensor additionally comprises a further recess.

15. The sensor system of claim 9, wherein the gas sensor is implemented as a metal oxide sensor.

16. The sensor system of claim 9, wherein the measuring area semiconductor body is implemented as a silicon component.

17. A sensor system for measuring a concentration of at least one gas from a gas sample, the sensor system comprising:

a carrier implemented as one of a ceramic carrier, a printed circuit board or a transistor outline header;

a measuring area semiconductor body implemented as a first micromechanical component;

a first gas sensor implemented as a second micromechanical component and comprising an electrode assembly, a sensitive layer and a sensor membrane that spans a recess, wherein the measuring area semiconductor body and the first gas sensor are connected to each other;

a second gas sensor with a further electrode assembly and a further sensitive layer; and a measuring area filled by the gas sample and arranged between the measuring area semiconductor body and the first gas sensor, wherein the gas sample in the measuring area is in contact with the first gas sensor and the second gas sensor, wherein the carrier has a carrier opening leading to the recess of the first gas sensor, wherein the carrier opening is configured to equalize pressure between the recess and surroundings of the sensor system, and wherein the sensor system is operable to:
initially heat up the measuring area by a heating device, and then switch off a heating or reduce a heating power to a value different from 0, and measure a change in resistance of the first and second gas sensors.

18. The sensor system of claim 17, wherein the first gas sensor comprises a sensor frame, wherein the recess is located in the sensor frame, and wherein the second gas sensor is arranged on the sensor frame.

19. The sensor system of claim 17, wherein the second gas sensor comprises a further sensor membrane, and wherein the second gas sensor additionally comprises a further recess.

20. The sensor system of claim 17, wherein the first gas sensor is implemented as a metal oxide sensor.

* * * * *